United States Patent [19]

Cassar et al.

[11] Patent Number: 4,540,791

[45] Date of Patent: Sep. 10, 1985

[54] PRODUCTION OF β-AMINO-α,β-UNSATURATED CARBOXYLIC ACID ESTERS

[75] Inventors: Luigi Cassar, Bologna, Italy; Abul Iqbal, Ettingen; Alain C. Rochat, Fribourg, both of Switzerland

[73] Assignee: Ciba-Geigy Corporation, Ardsley, N.Y.

[21] Appl. No.: 512,058

[22] Filed: Jul. 8, 1983

[30] Foreign Application Priority Data

Aug. 7, 1982 [CH] Switzerland ............... 4170/82

[51] Int. Cl.³ ............ C07D 211/70; C07C 101/02; C07C 121/78
[52] U.S. Cl. ............ 546/335; 260/465 D; 546/174; 548/375; 548/378; 548/495; 548/503; 549/77; 549/496; 560/38; 560/39
[58] Field of Search ............ 560/38; 260/465 D; 549/77, 496; 548/378, 495, 503; 546/330, 335, 174

[56] References Cited

U.S. PATENT DOCUMENTS 4,415,685 11/1983 Iqbal et al. ............... 524/92

OTHER PUBLICATIONS

J. Cason et al., J. Org. Chem., 18, 1594, (1953).
H. B. Kagan et al., Bull. Soc. Chim. Fr., 1966, 1819.
K. Maruoka et al., J. Am. Chem. Soc., 99, 7705, (1977).
L. Arsenijevic et al., Bull. Soc. Chim. Fr., 1968, 3403.
E. Santaniello et al., Synthesis, 1977, 698.
T. Iimori et al., Tetrahedron Letters, 27, 2525, (1979).
F. Dardoize et al., Bull. Soc. Chim. Fr., 10, 3841, (1972).
D. G. Farnum et al., Tetrahedron Letters, 29, 2549, (1974).
R. K. Howe et al., J. Heterocyclic Chem., 15, 1001, (1978).
T. Hiyama et al., Tetrahedron Letters, 23, 1597, (1982).

*Primary Examiner*—Dolph H. Torrence
*Attorney, Agent, or Firm*—Luther A. R. Hall

[57] ABSTRACT

A process for producing a compound of the formula

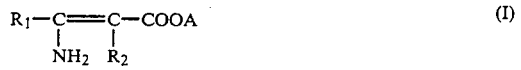

$$R_1-\underset{NH_2}{C}=\underset{R_2}{C}-COOA \quad (I)$$

wherein A is aryl or alkyl, $R_1$ is an aromatic radical and $R_2$ is hydrogen, alkyl, aryl, cyano, —COOalkyl or —COOaryl, which process comprises reacting 1 mol of an aromatic nitrile of the formula $R_1$—CN (II) with 1 mol of an acetic ester of the formula $(X)(R_2)CH$—COOA (III) in which X is halogen, in the presence of zinc, in an inert organic solvent and at a temperature of less than 80° C.; hydrolyzing in an alkaline medium the formed reaction product; and then isolating the compound of the formula I.

The compounds of the formula I are valuable intermediates for producing heterocyclic compounds.

10 Claims, No Drawings

PRODUCTION OF β-AMINO-α,β-UNSATURATED CARBOXYLIC ACID ESTERS

Various processes are known for producing β-amino-α,β-unsaturated carboxylic acid esters. Thus, for example, the production of β-aminocinnamic acid ethyl ester starting from cyanoacetic acid ethyl ester and a phenylmagnesium halide is described in the Journal of Heterocyclic Chemistry 15, 1001 (1978). However, the yields of β-amino-α,β-unsaturated carboxylic acid esters obtained by the known processes are inadequate. When, on the other hand, the starting materials chosen are an aromatic nitrile and a haloacetic acid ester, β-amino-α,β-unsaturated carboxylic acid esters are obtained in a very simple and economical manner, selectively and in high yield. The fact that the compounds aimed at can be produced with these starting materials is surprising. According namely to Tetrahedron Letters 23, 1597–1600 (1982), attempts made hitherto to produce a β-amino-α,β-unsaturated carboxylic acid ester from bromoacetic acid ethyl ester and benzonitrile have been unsuccessful.

The invention thus relates to a process for producing a compound of the formula I

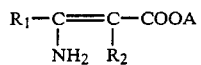  (I)

wherein A is alkyl or aryl, $R_1$ is an isocyclic or heterocyclic aromatic radical, and $R_2$ is hydrogen, alkyl, aryl, cyano or the group —COOZ, in which Z is alkyl or aryl, which process comprises reacting 1 mol of an aromatic nitrile of the formula

  (II)

with 1 mol of an acetic ester of the formula

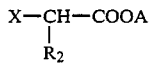  (III)

wherein X is halogen, in the presence of zinc, in an inert organic solvent and at a temperature of less than 80° C., hydrolysing in an alkaline medium the formed reaction product; and isolating the compound of the formula I for example by extraction.

When $R_1$ is an isocyclic aromatic radical, it is preferably a mono- to tetra-cyclic, especially mono- or bicyclic, radical, for instance phenyl, diphenylyl or naphthyl. If $R_1$ is a heterocyclic aromatic radical, then preferably it is a mono- to tricyclic radical. This can be purely heterocyclic, or can contain a heterocyclic ring and one or more fused-on benzene rings, for example thienyl, furyl, pyrrolyl, pyridyl, quinolyl, coumarinyl, benzofuranyl, benzimidazolyl or benzoxazolyl. Both the isocyclic and the heterocyclic aromatic radicals can have substituents as follows.

(1) Halogen atoms, for example chlorine, bromine or fluorine (2) Branched-chain or straight-chain alkyl groups having preferably 1 to 18, especially 1 to 12, particularly 1 to 8, and more especially preferred 1 to 4, C atoms. These alkyl groups can contain substituents, for example: fluorine, cyano, —OCOR$_3$, —OR$_4$, —COOR$_3$ or —CONR$_4$R$_5$, wherein R$_3$ is alkyl, aryl, such as phenyl or naphthyl, benzyl unsubstituted or substituted by halogen, alkyl or —O—alkyl, or it is a heterocyclic radical, R$_4$ and R$_5$ are alkyl which is unsubstituted or substituted by cyano, or they are C$_5$–C$_6$-cycloalkyl, aryl or heteroaryl, or R$_4$ and R$_5$ together with the N atom form a 5- or 6-membered hetero ring, for example a morpholine, piperidine or phthalimide ring. Further possible substituents on the alkyl groups are dialkylated amino groups, aryl groups, such as naphthylene, or in particular phenyl which is unsubstituted or substituted by halogen, alkyl or —O—alkyl, also heterocyclic aromatic radicals, such as the 2-thienyl, 2-benzoxazolyl, 2-benzthiazolyl, 2-benzimidazolyl, 6-benzimidazolonyl, 2-, 3- or 4-pyridyl, or 2-, 4- or 6-quinolyl radicals.

When the substituents stated under (2) for their part again contain alkyl, this alkyl can be branched-chain or straight-chain, and preferably contains 1 to 18, in particular 1 to 12, especially 1 to 8, and more especially 1 to 4, C atoms.

Examples of unsubstituted or substituted alkyl groups are: methyl, ethyl, n-propyl, isopropyl, n-butyl, sec-butyl, tert-butyl, tert-amyl, n-pentyl, n-hexyl, 1,1,3,3-tetramethylbutyl, n-heptyl, n-octyl, nonyl, decyl, undecyl, dodecyl, trifluoromethyl, trifluoroethyl, cyanomethyl, methoxycarbonylmethyl, acetoxymethyl or benzyl.

(3) The group OR$_6$, wherein R$_6$ is alkyl, aryl, for example naphthyl, or especially phenyl which is unsubstituted or substituted by halogen, alkyl or —O—alkyl, or it is C$_5$–C$_6$-cycloalkyl, aralkyl or a heterocyclic radical. Alkyl occurring in the definitions of R$_6$ can have e.g. one of the numbers of C atoms given under (2) as being preferred. Examples of R$_6$ which may be mentioned are: methyl, ethyl, n-propyl, isopropyl, trifluoroethyl, phenyl, o-, m- or p-chlorophenyl, o-, m- or p-methylphenyl, α-or β-naphthyl, cyclohexyl, benzyl, thienyl or pyranylmethyl.

(4) The group —SR$_6$, wherein R$_6$ has the meaning given under (3). Examples of R$_6$ which may be given are: methyl, ethyl, n-propyl, isopropyl, phenyl, o-, m- or p-chlorophenyl, o-, m- or p-methylphenyl, α-or β-naphthyl, cyclohexyl, benzyl, thienyl or pyranylmethyl.

(5) The cyano group.

(6) The group of the formula —NR$_4$R$_5$, wherein R$_4$ and R$_5$ have the meanings given under (2). Examples which may be mentioned are: dimethylamino, diethylamino, N,N-bis-(β-cyanoethyl)-amino, N-methylphenylamino, dibenzylamino, piperidyl or morpholyl.

(7) The group of the formula —COOR$_3$, wherein R$_3$ has the meaning given under (2). Examples of R$_3$ are: methyl, ethyl, isopropyl, n-butyl, tert-butyl, phenyl, benzyl or furfuryl.

(8) The group of the formula —NR$_7$COR$_3$, wherein R$_3$ has the meaning given under (2), and R$_7$ is alkyl, aryl, for example naphthyl, or particularly phenyl which is unsubstituted or substituted by halogen, alkyl or —O—alkyl, or it is C$_5$–C$_6$-cycloalkyl, aralkyl or the radical —COR$_3$, and two radicals —COR$_3$ together with the N atom can form a heterocyclic ring. Alkyl occuring in the definitions of R$_7$ can have for example one of the numbers of C atoms given under (2) as being preferred. Examples which may be given are: N-methylacetylamino, N-methyl-benzoylamino, N-succinimido or N-phthalimido.

(9) The group of the formula —NR₆COOR₃, wherein R₃ and R₆ have the meanings given under (2) and (3), respectively. As examples are mentioned the groups: —N(CH₃)COOCH₃, —N(phenyl)COOC₂H₅ or —N(CH₃)COC₆H₅.

(10) The group of the formula —NR₆CONR₄R₅, wherein R₆, R₅ and R₄ have the meanings given under (3) and (2). Examples which may be mentioned are: N,N,N'-trimethyl-ureido or N,N-dimethyl-N'-phenylureido.

(11) The groups of the formula —SO₂R₃ or —SOR₃, wherein R₃ has the meaning given under (2). Examples which may be given are: methylsulfonyl, ethylsulfonyl, phenylsulfonyl, 2-naphthylsulfonyl and phenylsulfoxidyl.

(12) The group of the formula —SO₂OR₃, wherein R₃ has the meaning given under (2). Examples of R₃ are: methyl, ethyl, phenyl, o-, m- or p-chlorophenyl, o-, m- or p-methylphenyl, or α- or β-naphthyl.

(13) The group of the formula —CONR₄R₅, wherein R₄ and R₅ have the meanings given under (2). Examples which may be given are: N,N-dimethylcarbamoyl, N-methyl-N-phenylcarbamoyl or N-piperidylcarbamoyl.

(14) The group of the formula —SO₂NR₄R₅, wherein R₄ and R₅ have the meanings given under (2). Examples which may be mentioned are: N-methyl-N-phenylsulfamoyl or N-morpholylsulfamoyl.

(15) The group of the formula —N=N—R₈, wherein R₈ is the radical of a coupling component, or a phenyl group which is unsubstituted or substituted by halogen, alkyl or —O—alkyl. Alkyl occurring in the definitions of R₈ can have for example one of the numbers of C atoms given under (2) as being preferred. Examples of R₈ which may be given are: pyrazolyl, pyridonyl or p-N,N-dimethylaminophenyl radicals.

(16) The group of the formula —OCOR₃, wherein R₃ has the meaning given under (2). Examples of R₃ are: methyl, ethyl, phenyl or o-, m- or p-chlorophenyl.

When A, R₂ and Z are alkyl, this can be branched-chain or straight-chain, and preferably contains 1 to 12, particularly 1 to 8, and more especially 1 to 5, C atoms. Examples of alkyl are: methyl, ethyl, n-propyl, isopropyl, n-butyl, sec-butyl, tert-butyl, n-pentyl, tert-amyl, n-hexyl, n-heptyl, n-octyl and 1,1,3,3-tetramethylbutyl.

Aryl denoted by A, R₂ and Z is in particular phenyl which is unsubstituted or phenyl substituted by halogen, such as chlorine, by $C_1$-$C_6$-alkyl, such as methyl, ethyl, isopropyl or tert-butyl, or by $C_1$-$C_6$-alkoxy, such as methoxy or ethoxy. Aryl is preferably unsubstituted phenyl.

X as halogen in the compound of the formula III can be for example chlorine, bromine or iodine, preferably bromine.

Starting materials preferably used in the process according to the invention are nitriles of the formula II wherein R₁ is unsubstituted or substituted phenyl or naphthyl.

Starting materials used in particular are nitriles of the formula IV

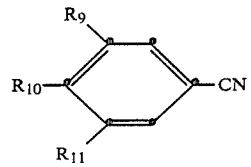

wherein R₉, R₁₀ and R₁₁ independently of one another are each hydrogen, halogen, cyano, trifluoromethyl, $C_3$-$C_{25}$-dialkylcarbamoyl, $C_1$-$C_{12}$-alkyl, $C_1$-$C_{12}$-alkoxy, $C_1$-$C_{12}$-alkylmercapto, $C_2$-$C_{13}$-alkoxycarbonyl, $C_3$-$C_{25}$-dialkanoylamino, $C_2$-$C_{24}$-dialkylamino; phenoxy, phenylmercapto, phenoxycarbonyl N—($C_1$-$C_{12}$)-alkyl-N-phenylcarbamoyl or N—($C_1$-$C_{12}$)-alkyl-N-benzoylamino, each unsubstituted or substituted on the phenyl by halogen, $C_1$-$C_{12}$-alkyl or $C_1$-$C_{12}$-alkoxy, at least one of the substituents R₉, R₁₀ and R₁₁ being hydrogen.

Starting materials more especially used are nitriles of the formula V

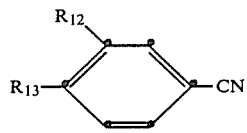

wherein one of the substituents R₁₂ and R₁₃ is chlorine, bromine, $C_1$-$C_4$-alkyl, cyano, $C_1$-$C_4$-alkoxy; phenoxy which is unsubstituted or substituted by chlorine or methyl, or is $C_3$-$C_9$-dialkylcarbamoyl; or N—($C_1$-$C_4$)-alkyl—N—phenylcarbamoyl which is unsubstituted or is substituted on the phenyl by chlorine, methyl or methoxy; and the other substituent is hydrogen.

Preferably used starting materials are compounds of the formula III wherein X is bromine or chlorine, A is $C_1$-$C_5$-alkyl or phenyl, and R₂ is hydrogen, $C_1$-$C_5$-alkyl, phenyl, cyano or the group —COOZ in which Z is $C_1$-$C_5$-alkyl or phenyl.

Particularly preferably used are compounds of the formula III wherein X is bromine or chlorine, A is methyl, ethyl, isopropyl or tert-butyl, and R₂ is hydrogen, methyl, ethyl or phenyl.

The process according to the invention is performed in the presence of zinc, and advantageously activated zinc is used. The activation of the zinc can be effected in a manner customarily used in organometallic chemistry; for example by treatment with a copper salt, such as copper acetate, in acetic acid, or with a mineral acid, such as hydrochloric acid or sulfuric acid.

The reaction of the ester of the formula III with the nitrile is performed in an inert organic solvent. Inert solvents are those which are not chemically changed under the reaction conditions. Suitable solvents are for example: ethers, such as tetrahydrofuran or dioxane; or glycol ethers, such as ethylene glycol dimethyl ether, ethylene glycol diethyl ether, diethylene glycol dimethyl ether or diethylene glycol diethyl ether; also aliphatic or aromatic hydrocarbons, such as benzene, or benzene substituted by alkyl, alkoxy or halogen, such as toluene, xylene, anisole or chlorobenzene. It is moreover also possible to use the nitrile of the formula II as solvent simultaneously, provided that it is liquid in the temperature range in which the reaction is carried out. The stated solvents can also be used as mixtures. There are advantageously used 1–20 parts by weight of solvent to 1 part by weight of the reactants.

The solvent preferably used in the process according to the invention is an ether or an aromatic hydrocarbon, especially ethylene glycol dimethyl ether, tetrahydrofuran, dioxane, anisole, benzene, toluene or o-, m- or p-xylene.

The reaction of the compound of the formula II with the compound of the formula III is performed at a temperature of less than 80° C., particularly at 0° to 80° C., especially at 20° to 50° C.

The reaction product is hydrolysed in an alkaline medium, the reaction solution being hydrolysed for example with aqueous alkali hydroxide, such as sodium, potassium or lithium hydroxide, or with an aqueous alkaline-earth hydroxide, such as calcium or magnesium hydroxide. To effect the hydrolysis, the aqueous alkali metal or alkaline-earth metal hydroxides are used preferably in such an amount that the reaction solution has a pH value of particularly 10 to 14, especially 13 to 14.

After hydrolysis, the β-amino-α,β-unsaturated carboxylic acid ester of the formula I can be extracted. Suitable for performing the extraction are organic solvents immiscible with water, for example diethyl ether, benzene, toluene, methylene chloride, chloroform or carbon tetrachloride. Also other processing methods familiar to a person skilled in the art are possible.

Even though it suffices as a rule to use the reactants in stoichiometric amounts, it can have a favourable effect on the yield when in particular the zinc is used in more than stoichiometric amounts, especially up to about 2.5 mols to 1 mol of the compound of the formula II.

A preferred embodiment of the process according to the invention is to place the nitrile of the formula II together with the metal into the reaction vessel, and to then add the compound of the formula III in controlled amounts. The rate of the controlled addition is adjusted in such a manner that the maximum temperature of 80° C. is not exceeded.

The compounds of the formulae II and III used as starting materials are known and can be produced by known processes.

By use of the process according to the present invention, the compounds of the formula I are as a rule obtained in a degree of purity sufficiently high to enable them to be further processed directly. The β-amino-α,β-unsaturated carboxylic acid esters of the formula I produced according to the invention are valuable intermediates.

These intermediates can be used, in a manner known per se, for the production of heterocycles, such as pyridenes (T. Kato et al., Yakugaku Zasshi, 91, 740 (1971); G. Hörlein et al., Liebigs Ann. Chem., 371 (1979)), pyrimidenes (K. Grohe et al., Liebigs Ann. Chem., 1025 (1973)), indoles (D. Raileannu et al., Tetrahedron, 27, 5031 (1971)) or isothiazoles (R. K. Howe et al., J. Heterocyclic Chem. 15, 1001 (1978)); or as thermostabilisers for PVC.

The compounds of the formula I wherein $R_2$ is hydrogen are suitable for producing pigments, particularly 1,4-diketopyrrolo-[3,4]-pyrroles, by for example reacting a compound of the formula I wherein $R_2$ is hydrogen firstly with a metal or metal salt, then with an aromatic nitrile and a haloacetic acid ester.

The Examples which follow further illustrate the invention.

EXAMPLE 1

0.75 g of $Cu(OCOCH_3)_2.H_2O$ is dissolved in 25 ml of glacial acetic acid at 90° C., and 13.1 g of zinc dust are then added. The mixture is stirred for 1 minute, decanted, and washed with glacial acetic acid and benzonitrile. The activated zinc is added to 25 ml of benzonitrile, and 0.05 g of iodine is introduced. There are subsequently added dropwise at 40° C. in a nitrogen atmosphere, in the course of 40 minutes, 9.3 ml of bromoacetic acid methyl ester. After completion of the dropwise addition, the mixture is stirred at 40° C. for 5 hours. The zinc still present is then filtered off. Ice-water is added to the filtrate, and the pH value is adjusted to 14 with aqueous sodium hydroxide solution. The mixture is afterwards extracted with chloroform, and the organic phase is washed neutral and dried over sodium sulfate. The product obtained is concentrated in a rotary evaporator and distilled under high vacuum. The yield is 13.9 g (78% of theory, relative to the bromoacetic acid methyl ester) of β-aminocinnamic acid methyl ester, which boils under 1.33 Pa at 105° C.

EXAMPLE 2

105 g of zinc dust (97.2%) are activated, according to Example 1, in glacial acetic acid with copper acetate, and then placed into 375 ml of benzonitrile. After the addition of 0.3 g of iodine, there is added dropwise within 1½ hours, with stirring, a mixture of 83.3 ml of bromoacetic acid ethyl ester and 150 ml of benzonitrile, the reaction temperature being maintained at 20°–25° C. After the dropwise addition is finished, the mixture is stirred at room temperature for a further 17 hours, and the zinc still present is then filtered off. The filtrate is poured into 1000 ml of water; the pH value is adjusted to 10–11 with 30% (by weight) aqueous sodium hydroxide solution, and stirring is continued for 1 hour. To the mixture are added 500 ml of diethyl ether, and the whole is stirred for a further 30 minutes. The organic phase is separated, washed neutral with water, and dried over sodium sulfate. The resulting product is concentrated in a rotary evaporator and distilled under high vacuum. The yield is 91.5 g (64% of theory) of β-aminocinnamic acid ethyl ester, which boils under 1.33 Pa at 120°–125° C.

EXAMPLE 3

When the procedure is carried out as in Example 2 except that non-activated zinc dust is used directly in place of the activated zinc, the procedure otherwise being the same, there is obtained in 38% yield likewise the β-aminocinnamic acid ethyl ester described under Example 2.

EXAMPLE 4

210 g of (97.2%) zinc dust are suspended in 250 ml of 2% (by weight) aqueous hydrochloric acid in an Erlenmeyer flask, and repeatedly shaken up for about 2 minutes. The suspension is subsequently filtered and the residue is washed neutral with water; it is then washed successively with ethanol, acetone and petroleum ether, and finally dried at 100° C. in a vacuum chamber. When this zinc activated with hydrochloric acid is used in Example 2 instead of the metal activated with glacial acetic acid, the procedure otherwise being analogous, β-aminocinnamic acid ethyl ester is obtained in 64% yield.

EXAMPLE 5

When fine zinc turnings, freshly scraped off on a lathe from zinc bars under nitrogen, are used in Example 2 in place of the zinc activated in glacial acetic acid, the reaction procedure and processing being otherwise analogous, β-aminocinnamic acid ethyl ester is obtained in 63% yield.

EXAMPLE 6

48.8 g of (97.2%) zinc dust are activated with hydrochloric acid according to Example 4, and are then placed into 170 ml of benzonitrile. After the addition of 0.14 g of iodine, there is added dropwise in the course of 1 hour, with stirring, a mixture of 51 ml of bromoacetic acid tert-butyl ester and 70 ml of benzonitrile, during which time the reaction temperature is held at 20°–25° C. Stirring is subsequently continued for 17 hours at room temperature. The processing of the reaction mixture is analogous to that described in Example 2. The yield is 53.8 g (71% of theory) of β-aminocinnamic acid tert-butyl ester which boils under 133 Pa at 154°–155° C.; m.p. 92° C.

EXAMPLE 7

21 g of (97.2%) zinc dust are treated, according to Example 4, with 2% (by weight) aqueous hydrochloric acid. The zinc activated in this manner is placed into 75 ml of diethylene glycol dimethyl ether, and 0.6 g of iodine is added. There is then added at 25° C. (if necessary with external cooling) a mixture of 16.7 ml of bromoacetic acid ethyl ester and 15.4 ml of benzonitrile. The mixture is stirred for 17 hours at room temperature, and subsequently processed basically analogously to Example 2. The β-aminocinnamic acid ethyl ester is obtained in 95% yield. When in the above Example the solvent diethylene glycol dimethyl ether is replaced by toluene or diethyl ether, the procedure being otherwise the same, there are likewise obtained good yields of β-aminocinnamic acid ethyl ester.

EXAMPLES 8–12

In a manner analogous to that of Example 7 are obtained further β-aminocinnamic acid derivatives of the general formula

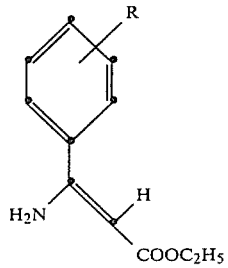

by reacting bromoacetic acid ethyl ester with the corresponding nitrile listed in column 2 of the following Table I. Column 3 shows the respective yields obtained.

TABLE I

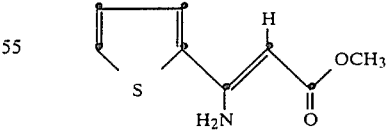

| Example No. | R | Yield (% of theory) | m.p. | b.p. |
|---|---|---|---|---|
| 8 | R = p-CH₃ | 64 | — | 122–123° C. at 10,6 Pa |
| 9 | R = p-Cl | 70 | — | 130–132° C. at 10,6 Pa |
| 10 | R = m-Cl | 65 | — | 124–125° C. at 8 Pa |
| 11 | R = p-CN | 87 | 83–85° C. | — |
| 12 | R = m-CN | 76 | 71–73° C. | — |

EXAMPLE 13

7.2 g of zinc dust (97.2%) are activated, according to Example 1, in glacial acetic acid with copper acetate, and are then placed into 25 ml of benzonitrile. After the addition of 0.05 g of iodine in a nitrogen atmosphere, there are added dropwise at 50° C., within 1 hour, 8.75 ml of chloroacetic acid methyl ester. After completion of the dropwise addition, the mixture is stirred at 65° C. for 15 hours, and the zinc then still present is filtered off. Ice-water is added to the filtrate, and the pH value is adjusted to 14 with aqueous sodium hydroxide solution. The mixture is extracted with ether; the ethereal phase is washed neutral and dried over sodium sulfate. The yield after subsequent distillation is 7.0 g (40% of theory, relative to the chloroacetic acid methyl ester) of β-aminocinnamic acid methyl ester.

EXAMPLE 14

13.1 g of (97.2%) zinc dust are activated, according to Example 1, in glacial acetic acid with copper acetate; the activated zinc dust is introduced into 25 ml of α-cyanothiophene, and 0.05 g of iodine is added. There are then added dropwise at 40° C. in a nitrogen atmosphere, within 40 minutes, 9.3 g of bromoacetic acid methyl ester. After completion of the dropwise addition, the mixture is stirred at 40° C. for 5 hours. The zinc still present is filtered off; ice-water is then added to the filtrate, and the pH value is adjusted to 14 with aqueous sodium hydroxide solution. The mixture is extracted with chloroform, and the organic phase is washed neutral and dried over sodium sulfate. Concentration in a rotary evaporator and distillation under high vacuum yield 9.1 g (50% of theory, relative to the bromoacetic acid methyl ester) of the compound of the formula Analysis: calculated: C 52.46%; H 4.92%; N 7.65%; found: C 52.12%; H 4.80%; N 7.41%.

EXAMPLE 15

13.1 g of (97.2%) zinc dust are activated, according to Example 1, in glacial acetic acid with copper acetate; the activated zinc is placed into 30 ml of 1,2-dimethoxyethane, and 0.05 g of iodine is added. There are then added at 20° C. (external cooling) in a nitrogen atmosphere, within 30 minutes, 9.3 g of bromoacetic acid methyl ester; and, in the course of 30 minutes, 10.4 g of 3-cyanopyridine are added. The mixture is stirred at 40° C. for 6 hours, and is subsequently processed as described in Example 1. The yield is 4.7 g (43% of theory, relative to the bromoacetic acid methyl ester) of the compound of the formula

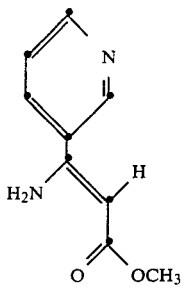

Analysis: calculated: C 60.67%; H 5.61%; N 15.73%; found: C 61.00%; H 5.50%; N 15.5%.

EXAMPLES 16-18

Analogously to Example 1 are obtained further β-aminocinnamic acid derivatives of the general formula

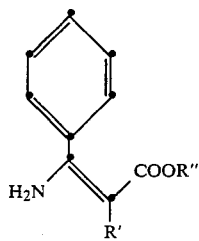

by reacting benzonitrile with the corresponding α-bromocarboxylic acid derivative given in column 2 of Table II. The columns 3 and 4 show the meanings of R' and R", and the respective product yields obtained are listed in column 5.

TABLE II

| Example No. | Bromocarboxylic acid derivative | R' | R" | Yield (% of theory) | m.p. or b.p. |
|---|---|---|---|---|---|
| 16 | CH₃—C(Br)—COOCH₃ | CH₃ | CH₃ | 62,5 | 97–98° C. at 0.015 mm |
| 17 | COOC₂H₅—C(Br)—COOC₂H₅ | C₂H₅ | C₂H₅ | 41 | 108.5° C. |
| 18 | C₆H₅—C(Br)—COOC₂H₅ | C₆H₅ | C₂H₅ | 27 | 69.1° C. |

EXAMPLE 19

0.8 g of Cu(OCOCH₃)₂.H₂O is dissolved in 25 ml of glacial acetic acid at 90° C., and 13.1 g of zinc dust are subsequently added. The mixture is stirred for 1 minute, decanted, and washed with glacial acetic acid and benzonitrile. The zinc is introduced into 50 ml of benzonitrile, and 0.05 g of iodine is added. There are then added 35.4 g of β-amino-p-chlorocinnamic acid methyl ester, and stirring is maintained at 20° to 25° C. for 2 hours. To this mixture are added 100 ml of p-xylene and 33.4 g of bromoacetic acid ethyl ester, and the whole is heated at 130° C. for 10 hours. The suspension is afterwards cooled; 50 ml of acetone are added, and the mixture is subsequently filtered. The yield after washing with glacial acetic acid and acetone and drying is 12.5 g of the pigment of the formula

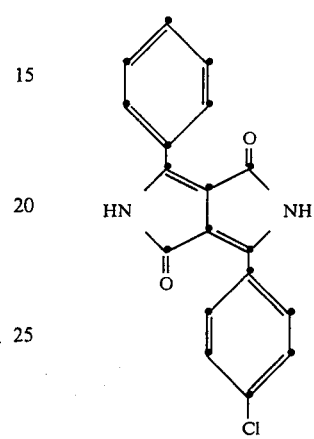

which, incorporated into PVC, gives a red dyeing.

Analysis: C₁₈H₁₁N₂O₂Cl  MW 322.5: calculated: C 66.99%; H 3.44%; N 8.68%; C 10.99%; found: C 66.50%; H 3.63%; N 8.54% C 10.40%.

λ$_{max}$ (nm) measured in dimethylformamide: 468/503.

What is claimed is:

1. An improved process for producing a compound of the formula

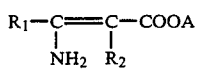

wherein
A is alkyl of 1 to 12 carbon atoms, phenyl or phenyl substituted by chlorine, by alkyl of 1 to 6 carbon atoms or by alkoxy of 1 to 6 carbon atoms, R₂ is hydrogen, alkyl of 1 to 12 carbon atoms, phenyl, phenyl substituted by chlorine, by alkyl of 1 to 6 carbon atoms or by alkoxy of 1 to 6 carbon atoms; cyano or the group —COOZ where Z is alkyl of 1 to 12 carbon atoms, phenyl or phenyl substituted by chlorine, by alkyl of 1 to 6 carbon atoms or by alkoxy of 1 to 6 carbon atoms, and R₁ is phenyl or said phenyl substituted by one or two fluorine, chlorine or bromine atoms or mixtures thereof, by one, two or three methoxy or methyl groups or mixtures thereof with chlorine atoms, by cyano, by amino, by dimethylamino, by hydroxyl, by trifluoromethyl, by alkoxycarbonyl of 2 to 3 carbon atoms, by tert-butyl, by cyanophenyl, by acetyl or by alkylbenzoyloxy of 11–14 carbon atoms; biphenylyl; naphthyl or said naphthyl substituted by methoxy or by amino; anthryl; phenanthryl; pyrazolyl or said pyrazolyl substituted by amino; pyridyl or said pyridyl substituted by methyl, hydroxy or by amyloxy; indolyl; quinolyl;

furyl or thienyl, by reacting equimolar amounts of a nitrile of formula II $$R_1CN \quad \text{(II)}$$

with an ester of formula III $$X-\underset{R_2}{CH}-COOA \quad \text{(III)}$$

wherein X is halogen, in the presence of zinc, in an inert organic solvent at a temperature of less than 80° C.,
the improvement comprising
hydrolyzing, the reaction product formed, in an alkaline medium; and
isolating the compound of formula I.

2. A process according to claim 1, where in the ester of formula III X is bromine or chlorine, A is $C_1$–$C_5$-alkyl or phenyl, and $R_2$ is hydrogen, $C_1$–$C_5$-alkyl, phenyl, cyano or the group —COOZ in which Z is $C_1$–$C_5$-alkyl or phenyl.

3. A process according to claim 1, where in the ester formula III X is bromine or chlorine, A is methyl, ethyl, isopropyl or tert-butyl, and $R_2$ is hydrogen, methyl, ethyl or phenyl.

4. A process according to claim 1, wherein activated zinc is used.

5. A process according to claim 1, wherein the zinc is used in more than stoichiometric amounts.

6. A process according to claim 1, wherein the inert organic solvent used is an aromatic hydrocarbon or an ether.

7. A process according to claim 1, wherein the reaction of the compound of the formula II with the compound of the formula III is performed at 20° to 50° C.

8. A process according to claim 1, wherein the alkaline hydrolysis is performed at a pH value of 10 to 14.

9. A process according to claim 1 wherein $R_1$ is phenyl or said phenyl substituted by chlorine, by methyl, by methoxy, by cyano; pyridyl; or thienyl.

10. A process according to claim 9 wherein $R_1$ is phenyl, 4-chlorophenyl, 3-methylphenyl, 3-cyanophenyl, 4-cyanophenyl, 3-pyridyl, or 2-thienyl.

* * * * *